US009919000B2

(12) United States Patent
Lytinas

(10) Patent No.: US 9,919,000 B2
(45) Date of Patent: Mar. 20, 2018

(54) ALTERING CANCER CELLULAR FUNCTIONS THROUGH PROTON MOPPING

(71) Applicant: Michael Theodore Lytinas, Boston, MA (US)

(72) Inventor: Michael Theodore Lytinas, Boston, MA (US)

( * ) Notice: Subject to any disclaimer, the term of this patent is extended or adjusted under 35 U.S.C. 154(b) by 138 days.

(21) Appl. No.: 14/479,619

(22) Filed: Sep. 8, 2014

(65) Prior Publication Data

US 2015/0072944 A1 Mar. 12, 2015

Related U.S. Application Data

(60) Provisional application No. 61/960,170, filed on Sep. 12, 2013.

(51) Int. Cl.
| | |
|---|---|
| *A01N 43/04* | (2006.01) |
| *A61K 31/70* | (2006.01) |
| *A61K 31/7028* | (2006.01) |
| *A61K 47/48* | (2006.01) |
| *A61K 31/7004* | (2006.01) |

(52) U.S. Cl.
CPC .... *A61K 31/7028* (2013.01); *A61K 47/48215* (2013.01); *A61K 31/70* (2013.01); *A61K 31/7004* (2013.01)

(58) Field of Classification Search
None
See application file for complete search history.

(56) References Cited

U.S. PATENT DOCUMENTS

2014/0378402 A1* 12/2014 Yano ...................... C07H 23/00
514/32

OTHER PUBLICATIONS

Brudzinska et al. Bioorganic & Medicinal Chemistry Letters (2004), vol. 14, pp. 2533-2536.*
Otman et al. Macromol. Chem. Phys. (2008), vol. 209, pp. 2410-2422.*
Fais Journal of Internal Medicine (2010), vol. 267, pp. 515-525.*
Swietach, P., Vaughan-Jones, R.D., Harris, A.L., Hulikova, A. "The chemistry, physiology and pathology of pH in cancer" *Phil. Trans. R. Soc.* B 369 20130099. The Royal Society (2014).
Supuran, Claudiu T. and Neri, Dario, "Interfering with pH regulation in tumours as a therapeutic strategy," Nature Reviews: Drug Discovery vol. 10 Macmillan Publishers Limited (2011).
Gerweck, Leo E. and Seetharaman, Kala. "Advances in Brief: Cellular pH Gradient in Tumor versus Normal Tissue: Potential Exploitation for the Treatment of Cancer" Cancer Research: 56, pp. 1194-1198 (1996).
Zhao R., Oxley D., Smith, T.S., Follows, G.A., Green, A.R., et al. "DNA damage-induced Bcl-xL deamidation is mediated by NHE-1 antiport regulated intracellular pH" PLoS Biol 5(1): e1 doi: 10.1371/journal.pbio.0050001. vol. 5 Issue 1 e1 Jan. 2007.

Gross, Liza "Manipulating cellular pH Suggests Novel Anticancer Therapy" doi:10,1371/journal.pbio.0050010 vol. 5 issue 1 e10 Jan. 2007.
Helmlinger, G., Sckell, A., Dellian, M. et al: Clinical Cancer Research "Acid Production in Glycolysis-impaired Tumors Provides New Insights into Tumor Metabolism" vol. 8, pp. 1284-1291 American Assoication for Cancer Reserach (2002).
Newell, K., Franchi, A., Pouyssegur, J., Tannock, I., "Studies with glycolysis-deficient cells suggest that production of lactic acid is not the only cause of tumor activity" Proc. natl. Acad. Sci. USA vol. 90 pp. 1127-1131 (1993).
P. Vaupel, F. Kallinowski and P. Okunieff—"Cancer Research: Blood Flow, Oxygen and Nutrient Supply, and Metabolic Microenvironment of Human Tumors: A Review" *Cancer Res* [1989;49:6449-6465].
Y. Masahiko, H. Shime, H. Hiromitsu et al; "IL-23-dependent and -independent enhancement pathways of IL-17A production by lactic acid" *International Immunology*, vol. 23, No. 1 pp. 29-41 doi: 10.1093/intimm/dxq455 Dec. 3, 2010.
LE Gerweck, SV Kozing and SJ Stocks; The pH partition theory predicts the accumulation and toxicity of doxorubicin in normal and low-pH-adapted cells. Article No. bjoc.1998.0134. British Journal of Cancer 79(5/6) pp. 838-842 1999.
P. Ebbesen, E. Petterson, T. Gorr et al; Informa Healthcare: Research Article—"Taking advantage of tumor cell adaptations to hypoxia for developing new tumor markers and treatment strategies" Journal of Enzyme Inhibition and Medicinal Chemistry, 2009; 24(S1): 1-39.
K. Yasumasa, S. Ozawa, C.Miyamoto et al; Cancer Cell International: Review—Open Access "Acidic extracellular microenvironment and cancer" BioMed Central Ltd. Dept. of Oral Function Molecular Biology Ohu University School of Dentistry, 963-8611, Koriyama, Japan 2013.
S. Hiroaki, M. Yabu, T. Akazawa, et al: The Journal of Immunology: "Tumor-Secreted Lactic Acid Promotes IL-23/IL-17 Proinflammatory Pathway" The American Associaton of Immunologists, Inc. Print ISSN: 0022-1767 Online ISSN: 1550-6606. (2008).
S. Mathupala, Y. H.Ko, P. Pedersen; Review: Biochimica et Biophysica Acta "The pivotal roles of mitochondria in cancer: Warbur and beyond and encouraging prospects for effective therapies" Journal Homepage: Apr. 8, 2010.
R. Gantenby and R. Gillies; "Why do cancers have high aerobic glycoloysis?" Nature Reviews: Cancer vol. 4 Nov. 2004.
HJ Park, JC Lyons, T. Ohtsubo and CW Song; "Acidic environment causes apoptosis by increasing caspase activity" British Journal of Cancer 80(12), 1892-1897 Article No. bjoc. (1999).

(Continued)

*Primary Examiner* — Patrick T Lewis
(74) *Attorney, Agent, or Firm* — Locke Lord LLP; Gabriel J. McCool

(57) ABSTRACT

Proton mopping is a new anti-cancer therapeutic approach that disrupts cancer's immunologic balance. It results in the alteration of the pHi/pHe ratio (intracellular-extracellular) of the cancer cell, leading cancer to either normalcy or apoptosis. This technology deploys a chemical compound that has two parts, a glucose part to guide the molecule to the cancer site and a proton neutralizer to mop up the protons. Proof of the validity of this therapeutic approach came after using an existing chemical compound 2-[2(2-Aminoethoxy) ethoxy]ethyl a-D-mannopyranoside, $C_{12}H_{25}NO_8$, which has the above mentioned properties. This compound is of the class of functionalized PEGylated glycosides, which are ligands for conjugation to biological molecules.

8 Claims, 2 Drawing Sheets

(56) References Cited

OTHER PUBLICATIONS

L. D. Shrode, H. Tapper and S. Grinstein; "Role of Intracellular pH in Proliferation, Transformation, and Apoptosis" Journal of Bioenergetics and Biomembranes, vol. 29, No. 4 (1997).
S. Jaekyoung, C. Lyssiotis, H. Ying et al: "Glutamine supports pancreatic cancer growth through a Kras-regulated metabolic pathway" Nature, 496(7443): 101-105, Apr. 4, 2013.
R. DeBerardinish and T. Cheng; "Q's next: The diverse functions of glutamine in metabolism, cell biology and cancer" Oncogene, 29(3) Jan. 21, 2010.
Y. Zhao, EB Butler and M. Tan; "Targeting cellular metabolism to improve cancer therapeutics" Cell Death and Disease macmillan Publishers Limited (2013).
P. Ward and C. Thompson; "Metabolic Reprogramming: A Cancer Hallmark Even Warburg Did Not Anticipate" Cancer Cell 21, Elsevier Inc. Mar. 20, 2012.
M. Vander Heiden, L.C. Cantley and C. B. Thompson; "Understanding the Warburg Effect: The Metabolic Requirements of Cell Proliferation" Science vol. 324 May 22, 2009.
R. J. Gillies, Z. Liu, and Z. Bhujwalla; "P-MRS measurements of extracellular pH of tumors using 3-aminopropylphosphonate" The American Physiological society (1994).
J. Chiche, M. Christiane Brahimi-Horn, J. Pouyssegur; "Tumour hypoxia induces metabolic shift causing acidosis: a common feature in cancer" Hypoxia Review Series: J. Cell. Mol. Med. vol. 14, No. 4 pp. 771-794 (2010).
R. A. Gatenby, E. T. Gawlinski, A.F. Gmitro et al; Acid-Mediated Tumor Invasion: a Multidisciplinary Study Research Article: Cancer Res 2006; 66:(10) May 15, 2006.
S. Reshkin, A. Belizzi, S. Caldeira et al; "$Na^+/H^+$exchanger-dependent intracellular alkalinization is an early event in malignant transformation and plays an essential role in the development of subsequent transformation-associated phenotypes" FASEB J.14, 2185-2197 (2000).
R. Gillies, R. Martinez-Zaguilan et al: "Tumorigenic 3T3 cells maintain an alkaline intracellular pH under physiological conditions" Proc. Natl. Acad. Sci. USA vol. 87, pp. 7414-7418, Oct. 1990.
J. Pouysségur, C. Sardet et al; "A specific mutation abolishing $Na^+/H^+$antiport activity in hamster fibroblasts precludes growth at neutral and acidic pH" Proc. natl. Acad. Sci. USA vol. 81, pp. 4833-4837, Aug. 1984.
Walter F. Boron; Refresher Course: Cellular Homeostasis -"Regulation of intracellular pH" Adv. Physiol Educ. 28: pp. 160-179, (2004).
Otto Warburg; "On the Origin of Cancer Cells" Science, New Series, vol. 123, No. 3191, pp. 309-314 (1956).
O. Warburg, F. Wind and E. Negelein; "The Metabolism of Tumors in the body" The Journal of General Physiology Mar. 7, 1927.
M. Macheda, S. Rogers and J. D. Best; "Molecular and Cellular Regulation of Glucose Transporter (GLUT) Proteins in Cancer" Journal of Cellular Physiology 202:654-662 (2005).
B. Webb, M. Chimenti et al; "Perspectives: Dysregulated pH: a perfect storm for cancer progression" Nature Reviews: Cancer vol. 11 Sep. 2011.

* cited by examiner

Figure 1: Histology
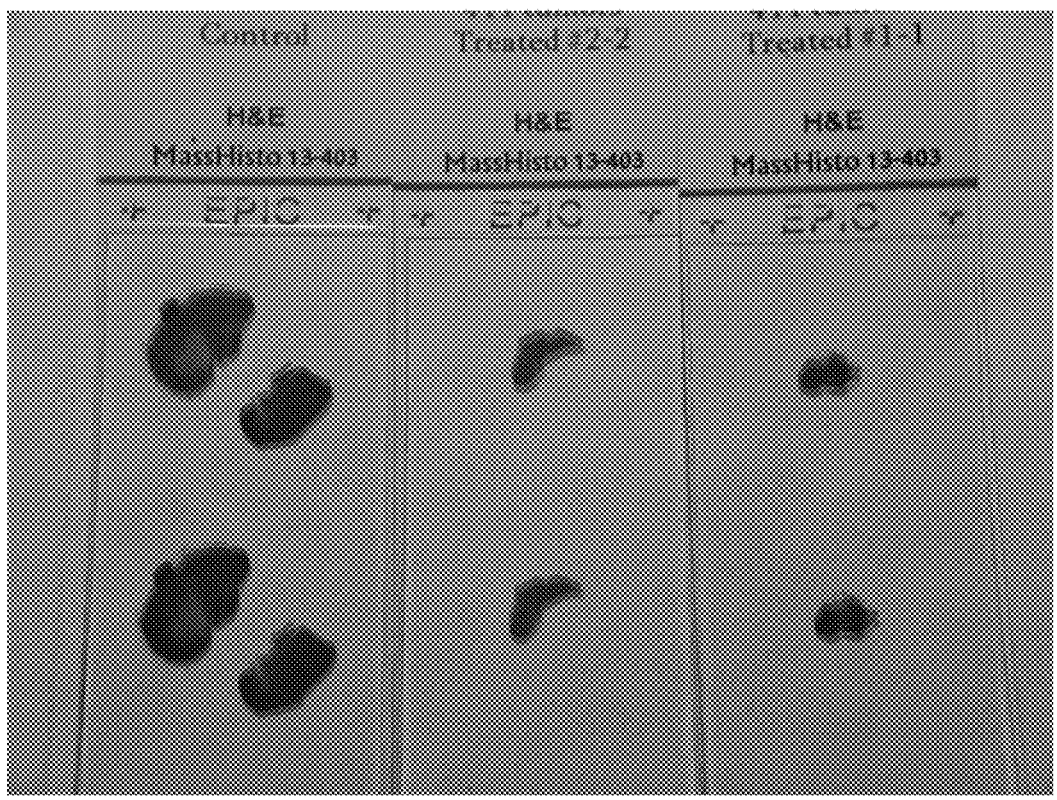
These histology slides show the untreated (control) group on the left and the treated group on the right. Gross size reduction was our goal. The maximal tumor growth inhibition index (T/C ratio) was around 48% (by day 10).

Figure 2: Measuring the Tumors
Measuring the gross size reduction of the tumor by using calipers was our biomarker.

ALTERING CANCER CELLULAR FUNCTIONS THROUGH PROTON MOPPING

RELATED APPLICATIONS

This application claims priority to U.S. Provisional Application No. 61/960,170, filed Sep. 12,2013, the entire contents of which are incorporated herein by reference.

BACKGROUND OF THE INVENTION

Field of the Invention

The present technology describes a new way of treating malignant solid tumors.

Related Art

Historically, cancer fighting has been about blocking, inhibiting or binding to specific molecular targets. It is either the classic chemotherapeutic approach or the targeted therapy or the immunological therapies. Taxol and 5-FU are both classic examples of the chemotherapeutic approach. Tamoxifen and Herceptin are examples of targeted therapies and Rituxan and Erbitux are examples of immunological therapies with monoclonal antibodies. All of these therapeutic approaches target either directly the cancer cell or rapidly dividing cells in various phases of division. The problem with the above mentioned therapeutic approaches is that they all have the cell or parts of the cell, as a target. However, the immense plasticity of cancer helps cancer to evade being treated as a target, therefore escaping treatment.

BRIEF SUMMARY OF THE INVENTION

In normalcy, the intracellular space is slightly acidic and the extracellular space is slightly alkaline. In cancer, this dogma is reversed. The intracellular space is slightly alkaline and the extracellular space is slightly or severely acidic. There is a new founded flow of hydrogen ions from the inside of the cancer cell to the outside due to overproduction of protons ($H^+$). This technology disrupts said cancer balance and changes the pH inside and outside of the cell. It does so by mopping the excess of protons that are produced by the cancer and guides the cancer cell back to normalcy or apoptosis. Fewer protons means altered pH and altered pH means altered cellular functions. In the case of cancer, it means back to normalcy or apoptosis. This way the suggested technology evades the immense plasticity of the cancer and treats cancer through its microenvironment.

FIG. 1: Histology slides of the experiments show the untreated (control) group on the left and the treated group on the right. Gross size reduction was our goal. The maximal tumor growth inhibition index (TIC ratio) was around 48% (by day 10).

FIG. 2: The gross size reduction of the tumor was measured by using calipers.

DETAILED DESCRIPTION OF THE INVENTION

What is the design of the chemical compound?

The chemical compound that is described by the new technology has two parts. The first part is a glucose molecule and the second part is a proton neutralizer. In this case, the proton neutralizer is an amine ($NH_2$). Said molecule needs two parts because it first needs to reach cancer and then deliver the proton mopping part.

What is the synthesis procedure of this chemical compound?

Synthesis of 1-(2-(2-(2-Aminoethoxy)ethoxy)ethoxy-D-mannopyranoside (5)

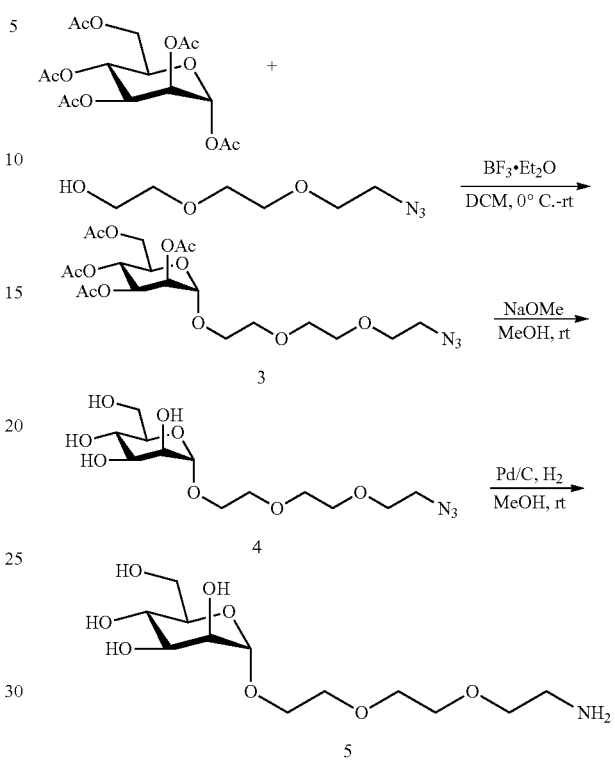

A solution of penta-O-acetate-α-D-mannopyranoside (300 mg, 0.77 mmol) and 2-(2-(2-azidoethoxy)ethoxy)ethanol (200 mg, 1.1 mmol) in dry dichloromethane (5 mL) was cooled to 0° C. $BF_3Et_2O$ (550 mg, 3.8 mmol) was added drop-wise, and the solution was stirred at rt overnight. The solution was poured into ice water, extracted with dichloromethane, and the extracts were washed with saturated $NaHCO_3$, brine and dried over $MgSO_4$. The crude product was purified by column chromatography on silica gel using hexane-ethyl acetate (1/1 v/v) as eluent, yielding compound 3 (152 mg, 43%) as a colorless oil. H-NMR (500 MHz, $CDCl_3$): δ 5.37 (dd, J=3.5 Hz, 1 H), 5.28 (d, J=9.5 Hz, 1 H), 5.26 (t, J=3.0 Hz, 1 H), 4.86 (d, J=1.0 Hz, 1 H), 4.28 (dd, J=5.0 Hz, 1 H), 4.10 (d, J=2.0 Hz, 1 H), 4.07 (m, 1 H), 3.81 (m, 1 H), 3.67 (m, 9 H), 3.39 (t, J=5.0 Hz, 2 H), 2.15 (s, 3 H), 2.10 (s, 3 H), 2.04 (s, 3 H), 1.99 (s, 3 H). C-NMR (125 MHz, $CDCl_3$): δ 170.8, 170.1, 170.03, 169.8, 97.8, 70.9, 70.8, 70.2, 70.2, 69.7, 69.2, 68.5, 67.5, 66.3, 62.5, 50.8, 21.0, 20.8, 20.8.

Compound 3 (128 mg, 0.24 mmol) was dissolved in dry methanol (2 mL), and NaOMe (6.8 mg, 0.12 mmol) was added. The reaction mixture was stirred at rt for 1 h. Amberlite IR-120 $H^+$ resin was added to adjust the pH to 7. The mixture was then filtered and the solvent was evaporated to yield compound 4 (92 mg, quant) as a colorless oil. H-NMR (500 MHz, $D_2O$): δ 4.88 (d, J=1.5 Hz, 1 H), 3.96 (dd, J=1.5 Hz, 1 H), 3.88 (m, 2H), 3.82 (m, 1 H), 3.71 (m, 9 H), 3.65 (m, 3 H), 3.50 (t, J=5.0 Hz, 2 H,). C-NMR (125 MHz, $D_2O$): δ 99.9, 72.7, 70.4, 69.9, 69.6, 69.5, 69.4, 69.2, 66.7, 66.3, 60.9, 50.1.

Compound 4 (82 mg, 0.24 mmol) was dissolved in dry methanol (3 mL), and Pd/C (23 mg) was added. The flask was purged with $N_2$ and filled with $H_2$. The mixture was stirred vigorously at rt for 1 h. The reaction mixture was then filtered through Celite and the solvent was evaporated to yield compound 5 (23 mg, 26%) as a clear oil. H-NMR (500 MHz, $D_2O$): δ 4.88 (s, 1 H), 3.95 (t, J=1.5 Hz, 1 H), 3.70 (m, 16H), 2.80 (t, J=5.5 Hz, 1 H,). C-NMR (125 MHz, $D_2O$): δ 99.9, 72.7, 70.4, 69.9, 69.6, 69.4, 69.3, 66.7, 66.3, 60.9, 47.4. MS (ESI): $[M+H]^+$ calculated for $C_{12}H_{25}NO_8$: 312.3, found: 312.1.

Why do we need two parts in this chemical compound?

The first part, the glucose, is needed to guide the compound to the cancer site. It is well known and established in the literature that the majority of solid tumors have an affinity for glucose consumption and they metabolize glucose either aerobically or anaerobically. This glucose part is the guidance system of the chemical compound. Example of a similar situation is the use of FDG to image cancer metastasis in the PET scan. The glucose part of the FDG (Fluoro-Deoxy-Glucose) is guiding the -in this case radioisotope for imaging- to the cancer sites. The second part is the actual proton neutralizer. In this case we use an amine ($NH_2$). This amine mops up a proton from inside the cancer cell and it becomes $NH_3$. That is how the disruption of the proton flow occurs and consequently how the pH modification occurs.

Where does this chemical compound enter the cell from?

Said chemical compound enters the cancer cell from the glucose receptors, especially the GLUT-1. Glucose receptors are over expressed in the majority of solid tumors, which facilitates the entrance of the glucose including molecule.

Which pathway does this chemical compound use, once inside the cell?

It uses the hexokinase pathway, the well-known and documented cellular glucose consumption metabolic pathway.

How does proton mopping alter cancer cellular functions?

By mopping the excess protons of the cancer's altered metabolism, this chemical compound alters the cancer's pHi/pHe ratio (intracellular-extracellular). It is of paramount importance to cancer to preserve said altered pHi/pHe in order to evade immunologic surveillance and to metastasize to other parts of the human body, as well as gain chemo and radio resistance (chemotherapy-radiotherapy). Cancer is so sensitive to this new pH ratio that even the slightest variation of this ratio, as low as 0.1 pH units or less, may disrupt important biochemical and/or biological processes such as ATP synthesis, enzyme function and the proliferation, migration, invasion and metastasis of tumor cells. Consequently, by altering this pH ratio, cancer is guided back to either normalcy or apoptosis.

Who else talks about pH manipulation as a cancer therapy?

1. The chemistry, physiology and pathology of pH in cancer
   Pawel Swietach, Richard D. Vaughan-Jones, Adrian L. Harris and Alzbeta Hulikova Phil. Trans. Royal Society B 2014 369, 20130099, published 3 Feb. 2014
2. Interfering with pH regulation in tumours as a therapeutic strategy
   Dario Neri and Claudiu T. Supuran NATURE REVIEWS | DRUG DISCOVERY VOLUME 10 | OCTOBER 2011 | 767
3. Dysregulated pH: a perfect storm for cancer progression
   Bradley A. Webb, Michael Chimenti, Matthew P. Jacobson and Diane L. Barber NATURE REVIEWS | CANCER VOLUME 11 | September 2011 | 671
4. Cellular pH gradient in tumor versus normal tissue: potential exploitation for the treatment of cancer
   Leo E. Gerweck and Kala Seetharaman CANCER RESEARCH 56, 1194-1198, Mar. 15, 1996
5. DNA Damage-Induced Bcl-xL Deamidation Is Mediated by NHE-1 Antiport Regulated Intracellular pH
   Rui Zhao, David Oxley, Trevor S. Smith, George A. Follows, Anthony R. Green, Denis R. Alexander PLoS Biology | www.plosbiology.org 0039 January 2007 | Volume 5 | Issue 1 | e1
6. Influence of Tumor pH on Therapeutic Response
   Chang W. Song, PhD, Robert Griffin, PhD, and Heon Joo Park, MD, PhD
   From: Cancer Drug Discovery and Development: Cancer Drug Resistance Edited by: B. Teicher© Humana Press Inc., Totowa, N.J.

Who else uses PEGylated glycosides to deliver therapeutic molecules?

1. U.S. Pat. No. 8,063,015 B2,
2. US 2003/0031671 A1

Both patents and their references are about using several PEGylated glycosides as a vehicle to deliver either monoclonal antibodies or other therapeutic molecules to cancer.

How does this technology differ from other cancer therapies?

The suggested technology does not target the cancer cell per se like all other technologies do. The immense plasticity of the cancer cells makes it very hard for other therapeutic approaches to guide cancer to a different state. The suggested technology deals with the micro environment that cancer creates to favor its survival. This micro environment is the altered pH ratio from inside and outside of the cell. By disrupting this micro environment, which is manifested by the cancer's new pHi/pHe ratio, the new technology evades cancer's immense plasticity by not directly dealing with the cancer cells themselves. In contrast, all the existing technologies target cancer cells in an attempt to kill them. In the classic chemotherapeutic approach, the target is all rapidly dividing cells, which includes normal cells, hence the tremendous side effects.

How do we know that this technology with said compound works?

There are preliminary clinical results in mice that prove that the compound of the suggested technology works on a syngeneic mouse breast cancer model.

[FIG. 1] This is the human breast cancer analog, which shows 48% tumor reduction. (The protocol of the experiment follows in the next page)

Protocol of the Experiment

The Purpose: to assess the anti-tumor activity of the existing compound, $C_{12}H_{25}NO_8$, PEGylated amine functionalized glycoside, 2-[2(2-Aminoethoxy)ethoxy]ethyl a-D-mannopyranoside, on a model of mouse 4T1 breast tumor in Balb/C mice.

Animal and Facility: healthy female Balb/c (5-6 weeks old), purchased from Harlan Laboratories, were allowed to acclimate for 3 days in a specific pathogen free animal facility. Animal housing, handling and procedures were followed according to the protocols and guidelines approved by the lab's Institutional Animal Care and Use Committee (IACUC).

In Vivo Syngeneic Tumor Study Design: Murine 4T1 breast tumor cells were kept in RPMI-1640 medium containing 10% FBS and 1% Pen/Strep. On the day of inoculation, the cells were harvested according to standard protocol (Beth Pulaski) and re-suspended in PBS at the cell concentration of 2.5×105 cells/ml. Each animal was injected with 0.1 ml of the cell solution into the right flank of Balb/c mice following the SOP. On the 8th day post-inoculation, all tumor volumes were measured and the animals were divided into two groups, control and treated.

Study Design: to deliver a predetermined dose of the compound intravenously for 5 days.

Study Objective: to observe clinically the reduction of the size of the tumors using calipers (our "biomarker").[FIG. 2]

Treatment: the tested compound was prepared right before dosing on day 8 after 4T1 inoculation. Each mouse received a predetermined dose of either the compound or saline intravenously daily for 5 consecutive days. The mice tumor volumes and mice body weights were monitored every other day along with other general behavior factors.

Endpoints: animal was euthanized if one of the following conditions was identified:
  its neoplasm reached the predetermined 1000 cubic mms
  the animal became moribund
  body weight lost more than 20% of its original weight Results: In the study, the 4T1 tumor growth was similar to our previous data. The control tumors were doubled every 2-3 days. However, the tumors in the treated group with the compound grew slowly. This means that the compound can inhibit 4T1 tumor growth during treatment (from day 8 to day 12). In fact, the maximal tumor growth inhibition index (TIC ratio) was around 48% (by day 10) [FIG. 1]. The inhibitory effect on the tumor growth by the compound was tolerated by the mice and no toxic effects were observed.

The invention claimed is:

1. A method for treating a solid breast tumor, comprising administering a therapeutically effective amount of a compound comprising a tumor targeting moiety linked to a proton neutralizing moiety by a linker, wherein the targeting moiety is glucose, the linker is PEG, and the proton neutralizing moiety is an amine ($NH_2$).

2. The method according to claim 1, wherein the administering comprises local administration directly to the breast tumor.

3. The method according to claim 1, wherein the administering comprises intravenous injection.

4. The method according to claim 1, wherein the therapeutically effective amount is sufficient to reduce the size of the solid breast tumor.

5. The method according to claim 4, wherein the solid breast tumor is reduced by up to 48%.

6. The method according to claim 1, wherein the therapeutically effective amount is sufficient to alter the pHi/pHe ratio of the solid tumor to a normal pHi/pHe ratio.

7. The method according to claim 6, wherein the pHi/pHe ratio is altered by at least 0.1 pH units.

8. The method according to claim 1, wherein the therapeutically effective amount is sufficient to cause the solid breast tumor to revert to normalcy or to enter apoptosis.

* * * * *